(12) United States Patent
Wang

(10) Patent No.: US 11,752,048 B2
(45) Date of Patent: Sep. 12, 2023

(54) DISPOSABLE ABSORPTION PRODUCT AND ABSORBABLE CORE

(71) Applicant: Fujian Yongrongda Daily Necessities Manufacturing Co., Ltd., Fujian (CN)

(72) Inventor: Xusheng Wang, Fujian (CN)

(*) Notice: Subject to any disclaimer, the term of this patent is extended or adjusted under 35 U.S.C. 154(b) by 374 days.

(21) Appl. No.: 17/216,787

(22) Filed: Mar. 30, 2021

(65) Prior Publication Data
US 2021/0378886 A1    Dec. 9, 2021

(30) Foreign Application Priority Data

Jun. 5, 2020 (CN) .......................... 202010506931.4

(51) Int. Cl.
  *A61F 13/537* (2006.01)
  *A61F 13/534* (2006.01)
  *A61F 13/15* (2006.01)
  *A61F 13/53* (2006.01)

(52) U.S. Cl.
CPC .. *A61F 13/53713* (2013.01); *A61F 13/53747* (2013.01); *A61F 2013/15365* (2013.01); *A61F 2013/5349* (2013.01); *A61F 2013/530226* (2013.01); *A61F 2013/530605* (2013.01); *A61F 2013/53769* (2013.01); *A61F 2013/53782* (2013.01); *A61F 2013/530802* (2013.01); *A61F 2013/530927* (2013.01)

(58) Field of Classification Search
CPC .............. A61F 13/53; A61F 2013/5349; A61F 2013/15365; A61F 2013/530226; A61F 2013/530927; A61F 2013/53769; A61F 13/53713; A61F 13/53747; A61F 2013/530605; A61F 2013/530802; A61F 2013/53782

USPC ................................................. 604/358–392
See application file for complete search history.

(56) References Cited

U.S. PATENT DOCUMENTS

| | | | |
|---|---|---|---|
| 2003/0087086 A1* | 5/2003 | Koslow | D06N 3/0056 428/323 |
| 2003/0135179 A1* | 7/2003 | Krautkramer | D04H 1/559 604/374 |

FOREIGN PATENT DOCUMENTS

| | | | |
|---|---|---|---|
| CN | 213489841 U | * | 6/2021 |
| JP | 2019005421 A | * | 1/2019 |
| JP | 2019051104 A | * | 4/2019 |

* cited by examiner

*Primary Examiner* — Susan S Su

(57) ABSTRACT

An absorbable core of a disposable absorption product, having an upper polyurethane foam layer which is liquid-permeable and a wrapping layer which is capable of absorbing liquid; the wrapping layer comprises an outer part and an inner part; the outer part is a first liquid-permeable sleeve body; the inner part is an accommodating cavity; a lower polyurethane foam layer and a particle layer are provided inside the accommodating cavity; the particle layer is distributed on an upper surface of the lower polyurethane foam layer and is formed by resin particles, organic acid particles and anhydrous bicarbonate particles mixed together. A disposable absorption product comprising said absorbable core is also provided. By integrating polyurethane polymer foam with superabsorbent polymer particles, organic acid particles and anhydrous bicarbonate particles, the absorbable core is good at absorbing and locking liquid, and provides soft and elastic supporting materials which provide great comfort to users.

10 Claims, 2 Drawing Sheets

DISPOSABLE ABSORPTION PRODUCT AND ABSORBABLE CORE

BACKGROUND OF THE INVENTION

The invention relates to the technical field of sanitary products, in particular to a disposable absorption product and absorbable core.

A absorbable core for absorbing human and animal excrement commonly available in the market are roughly classified into three types, namely, a wood pulp core, a composite absorbable paper and a nonwoven composite core, wherein the wood pulp core is made of pulverized fluff pulp/wood pulp wrapped by nonwoven fabrics or airlaid paper; the composite absorbable paper is made by pressing and bonding viscose fiber, fluff pulp/wood pulp and acrylic acid-based super-absorbable polymer particles; the nonwoven composite core is made of multiple layers of nonwoven fabrics and super-absorbable polymer particles adhered together by hot melt adhesive. However, the absorbable cores of the prior art have to be laminated multiple times during production, and so fibers in the absorbable cores after lamination are accumulated and hardened, therefore the absorbable cores may not provide a sufficiently soft feeling to users during the process of use, and in addition, the absorbable cores are very hard that the absorption product cannot be well attached to the part that requires absorption, therefore easily resulting in leakages such as side leakage.

BRIEF SUMMARY OF THE INVENTION

The invention provides a disposable absorption product which is soft, elastic, super-absorbable and comfortable to use.

The purpose of the invention is realized by the following scheme:

Scheme One

An absorbable core of a disposable absorption product, wherein the absorbable core comprises an upper part and a lower part; the upper part is an upper polyurethane foam layer which is liquid-permeable; the lower part is a wrapping layer which is capable of absorbing liquid;

the wrapping layer comprises an outer part and an inner part; the outer part is a first sleeve body which is liquid-permeable; the inner part is an accommodating cavity; a lower polyurethane foam layer and a particle layer are provided inside the accommodating cavity, wherein the particle layer is evenly distributed on an upper surface of the lower polyurethane foam layer and is formed by resin particles, organic acid particles and anhydrous bicarbonate particles mixed together; the resin particles are distributed on the upper surface of the lower polyurethane foam layer according to an amount of 50-150 $g/m^2$, the organic acid particles are distributed on the upper surface of the lower polyurethane foam layer according to an amount of 15-25 $g/m^2$, and the anhydrous bicarbonate particles are distributed on the upper surface of the lower polyurethane foam layer according to an amount of 8-16 $g/m^2$.

In the absorbable core of the disposable absorption product according to the present scheme, the resin particles are super-absorbable high molecular polymer particles (commonly known as SAP—super-absorbable polymer). The absorbable core comprising said resin particles has super liquid absorption capacity and super liquid locking capacity. The absorbable core of the present scheme contains solid organic acid particles and anhydrous bicarbonate particles. When water content of the liquid in human excrement contacts the solid organic acid particles and the anhydrous bicarbonate particles, the organic acid particles and the anhydrous bicarbonate particles are dissolved in water to obtain a water solution, and then the organic acid and the bicarbonate react in the water solution to generate gaseous carbon dioxide. The generated gaseous carbon dioxide escapes from a space formed between a lower surface of the upper polyurethane foam layer and an upper surface of the lower polyurethane foam layer, passes through the upper polyurethane foam layer, and then contacts with the excretory organs of the human body. As such, the temperature and humidity of the contacted parts of the excretory organs can be reduced, and the generated flow of gaseous carbon dioxide may soothe the outer surfaces of the excretory organs to increase comfortability.

Further, a molar ratio of the organic acid particles to the anhydrous bicarbonate particles is 1:1. The resin particles are super-absorbable polymer resin particles.

Further, the first sleeve body is made of hydrophilic non-woven fabric or toilet paper.

Further, the lower surface of the upper polyurethane foam layer and/or the upper surface of the lower polyurethane foam layer is/are undulated.

An upper surface of the upper polyurethane foam layer is a nearly flat plane and a lower surface of the lower polyurethane foam layer is a nearly flat plane. The lower surface of the upper polyurethane foam layer is an undulated surface, and the upper surface of the lower polyurethane foam layer is an undulated surface. Accordingly, in the finally obtained absorption product, a space which contains air is formed between the lower surface of the upper polyurethane foam layer and the upper surface of the lower polyurethane foam layer; part of the wrapping layer, the particles and the air are contained in the space. Therefore, after human excrement enters the space through a top sheet and the upper polyurethane foam layer, the human excrement not only permeates downwards along a direction perpendicular to the absorption product, but also transversely diffuses along a direction parallel to the absorption product, so that the permeation speed of liquid in the human excrement is increased, thereby keeping an upper surface of the top sheet dry.

Further, the upper polyurethane foam layer comprises a continuous and uniform first porous foam block made of hydrophilic polyurethane material, and a first non-woven fabric layer provided inside the first porous foam block and extending through said first porous foam block along an extending direction of a planar surface of the first porous foam block. The first non-woven fabric layer is arranged in the first porous foam block to compensate the tensile strength of the foam, thereby increasing the tensile strength.

Further, for faster liquid absorption, the upper polyurethane foam layer is provided with a plurality of through holes penetrating through an upper surface and a lower surface of the first porous foam block.

Further, the lower polyurethane foam layer comprises a continuous and uniform second porous foam block made of hydrophilic polyurethane material, and a second non-woven fabric layer provided inside the second porous foam block and extending through said second porous foam block along an extending direction of a planar surface of the second porous foam block. The second non-woven fabric layer is arranged in the second porous foam block body to compensate the tensile strength of the foam, thereby increasing the tensile strength.

Preferably, the absorbable core has a thickness of 0.8 mm to 6 mm.

Preferably, the absorbable core has a thickness of 0.8 mm to 2.5 mm.

Scheme Two

A disposable absorption product, comprising a liquid-permeable top sheet at a top side of the disposable absorption product, a liquid-impermeable bottom sheet at a bottom side of the disposable absorption product, and an absorbable core according to any one of claims 1-8; the absorbable core is sandwiched between the top sheet and the bottom sheet.

The disposable absorption product further comprises a leakproof layer which is bonded to an outer edge of the absorbable core and is connected to an upper surface of the top sheet and an upper surface of the bottom sheet.

Furthermore, a lower surface of the top sheet and the upper surface of the upper polyurethane foam layer, the lower surface of the upper polyurethane foam layer and an outer surface of the wrapping layer, the upper surface of the lower polyurethane foam layer and an inner surface of the wrapping layer, as well as the outer surface of the wrapping layer and the upper surface of the bottom sheet are each bonded by hot melt adhesive.

The absorbable core is still soft after lamination due to the use of soft and elastic polyurethane foam. As a result, the disposable absorption product of the present invention has super liquid absorbing capacity, and it is also soft and can be well attached to a body part that requires liquid absorption, furthermore, it will not cause leakages such as side leakage.

The invention has the following beneficial effects: the present invention uses polyurethane foam to replace supporting materials such as fluff pulp/wood pulp, viscose fiber, fluffy non-woven fabric and the like used in the absorbable core according to the prior art, and the present invention integrates the polyurethane foam with super-absorbable polymer particles, organic acid particles and anhydrous bicarbonate particles to provide soft and elastic supporting materials having sufficiently good capacity of liquid absorption and locking. Accordingly, when using the present invention, the user can enjoy the comfortable feeling like lying on a sponge mattress or on a sponge sofa.

The structure and materials of the present invention make the present invention soft and elastic, and thus can be better attached to a body part that requires liquid absorption. The present invention can also prevent leakages such as side leakage, thereby being more convenient and safer to use.

The absorption product of the present invention contains solid organic acid particles and anhydrous bicarbonate particles. After the absorption product absorbs liquid in human excrement, the solid organic acid particles and the anhydrous bicarbonate particles are dissolved in the liquid solution and react with each other to generate gaseous carbon dioxide. The generated gaseous carbon dioxide enters the area surrounding the human excretory organs through the top sheet in form of a breeze to relieve the stuffiness feeling surrounding the human excretory organs.

BRIEF DESCRIPTION OF THE DRAWINGS

In order to more clearly illustrate the technical solutions provided by the embodiments of the present invention or by the prior art, the drawings required to be used in the description of the embodiments or the prior art will be briefly described below, it is obvious that the drawings in the following description are intended to illustrate only some embodiments of the present invention, and other drawings can be obtained by those skilled in the art based on the drawings described herein without any inventive efforts. In the drawings.

DETAILED DESCRIPTION OF THE INVENTION

Figure 1:
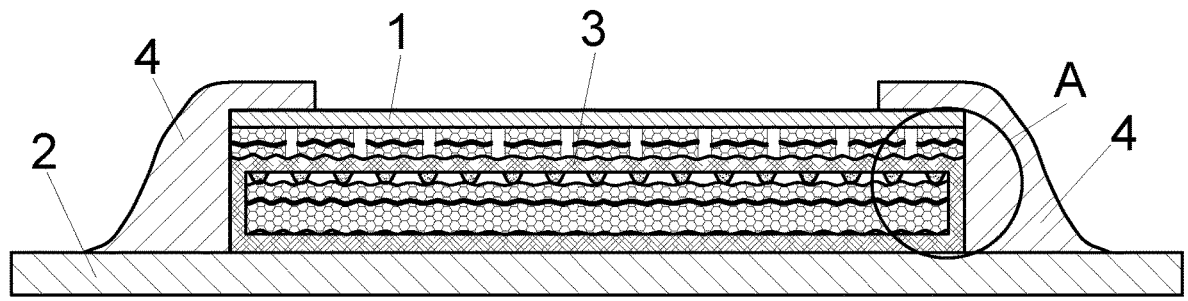
FIG. 1 is a schematic sectional structural view of the present invention.
Figure 2:
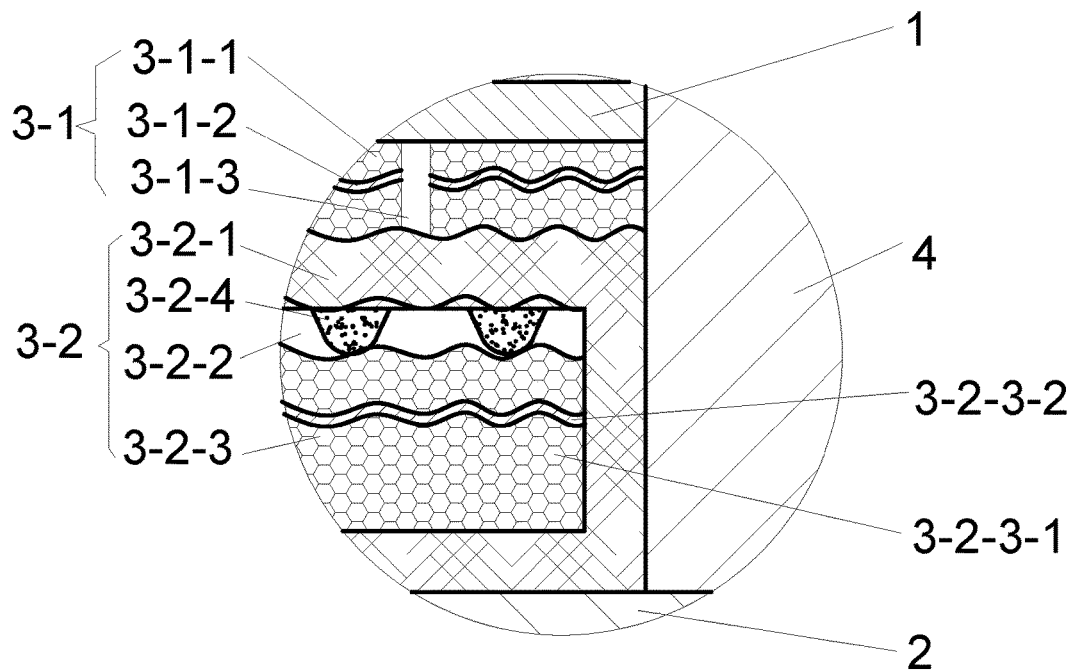
FIG. 2 is a partially enlarged view of FIG. 1 at area A.
Figure 3:
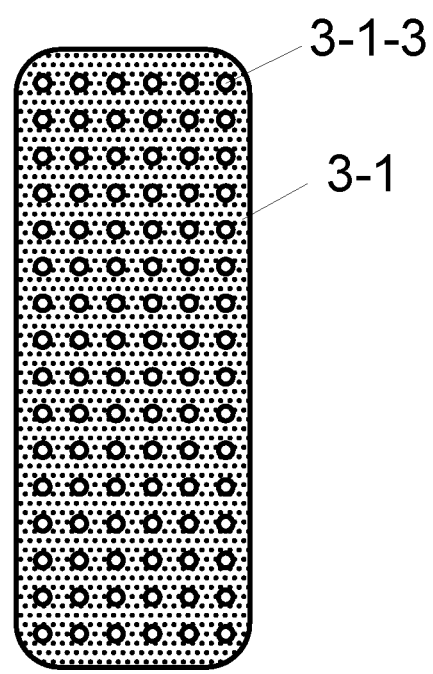
FIG. 3 is a top view of the upper polyurethane foam layer.

The technical solutions in the embodiments of the present invention will be clearly and completely described below with reference to the drawings in the embodiments of the present invention.

In the description of the present invention, it is to be understood that the terms "center", "longitudinal", "lateral", "length", "width", "thickness", "upper", "lower", "front", "rear". "left", "right", "vertical", "horizontal", "top", "bottom", "inner", "outer", "etc. indicate orientations or positional relationships based on those shown in the drawings, merely for convenience of description and simplicity of description, and do not indicate or imply that the device or element referred to must have a particular orientation, be constructed and operated in a particular orientation, and thus, are not to be construed as limiting the invention.

Furthermore, the terms "first" and "second" are used for descriptive purposes only and are not to be construed as indicating or implying relative importance or to implicitly indicate the number of technical features indicated. Thus, a feature defined as "first" or "second" may explicitly or implicitly include one or more of that feature. In the description of the present invention, "a plurality" means two or more unless specifically defined otherwise.

An absorbable core of a disposable absorption product, the absorbable core comprises an upper part and a lower part; the upper part is an upper polyurethane foam layer (3-1) which is liquid-permeable; the lower part is a wrapping layer (3-2) which can absorb liquid;

The wrapping layer (3-2) comprises an outer part and an inner part; the outer part is a first sleeve body (3-2-1) which is liquid-permeable; the inner part is an accommodating cavity (3-2-2); a lower polyurethane foam layer (3-2-3) and a particle layer (3-2-4) are provided inside the accommodating cavity (3-2-2), wherein the particle layer (3-2-4) is evenly distributed on an upper surface of the lower polyurethane foam layer (3-2-3) and is formed by resin particles, organic acid particles and anhydrous bicarbonate particles evenly mixed together. The resin particles are distributed on the upper surface of the lower polyurethane foam layer (3-2-3) according to an amount of 50-150 $g/m^2$, the organic acid particles are distributed on the upper surface of the lower polyurethane foam layer (3-2-3) according to an amount of 15-25 $g/m^2$, and the anhydrous bicarbonate particles are distributed on the upper surface of the lower polyurethane foam layer (3-2-3) according to an amount of 8-16 $g/m^2$.

The absorbable core of the disposable absorption product has super liquid absorption capacity and super liquid locking capacity, containing solid organic acid particles and anhydrous bicarbonate particles. When water content of the liquid in human excrement contacts the solid organic acid particles and the anhydrous bicarbonate particles, the organic acid particles and the anhydrous bicarbonate particles are dissolved in water to obtain a water solution, and then the organic acid and the bicarbonate react in the water solution to generate gaseous carbon dioxide. The generated gaseous carbon dioxide escapes from a space formed between a lower surface of the upper polyurethane foam layer and an upper surface of the lower polyurethane foam layer, passes through the upper polyurethane foam layer, and then contacts with the excretory organs of the human body. As such, the temperature and humidity of the contacted parts of the excretory organs can be reduced, and the generated flow of gaseous carbon dioxide may soothe the outer surfaces of the excretory organs to increase comfortability.

Further, a molar ratio of the organic acid particles to the anhydrous bicarbonate particles is 1:1. The resin particles are super-absorbable polymer resin particles.

Further, the lower surface of said upper polyurethane foam layer (3-1) and/or the upper surface of said lower polyurethane foam layer (3-2-3) is undulated.

An upper surface of the upper polyurethane foam layer may be a nearly flat plane and a lower surface of the lower polyurethane foam layer may be a nearly flat plane. The lower surface of the upper polyurethane foam layer is an undulated surface, and the upper surface of the lower polyurethane foam layer is an undulated surface. Accordingly, in the finally obtained absorption product, a space which may contain air is formed between the lower surface of the upper polyurethane foam layer and the upper surface of the lower polyurethane foam layer; part of the wrapping layer, the particles and the air are contained in the space. Therefore, after human excrement enters the space through a top sheet and the upper polyurethane foam layer, the human excrement not only permeates downwards along a direction perpendicular to the absorption product, but also transversely diffuses along a direction parallel to the absorption product, so that the permeation speed of liquid in the human excrement is increased, thereby keeping an upper surface of the top sheet dry.

Further, the upper polyurethane foam layer (3-1) comprises a continuous and uniform first porous foam block (3-1-1) made of hydrophilic polyurethane material, and a first non-woven fabric layer (3-1-2) provided inside the first porous foam block (3-1-1) and extending through said first porous foam block (3-1-1) along an extending direction of a planar surface of the first porous foam block (3-1-1).

Further, for faster liquid absorption, the upper polyurethane foam layer (3-1) is provided with a plurality of through holes (3-1-3) penetrating through an upper surface and a lower surface of the first porous foam block.

Further, the lower polyurethane foam layer (3-2-3) comprises a continuous and uniform second porous foam block (3-2-3-1) made of hydrophilic polyurethane material, and a second non-woven fabric layer (3-2-3-2) provided inside the second porous foam block (3-2-3-1) and extending through said second porous foam block (3-2-3-1) along an extending direction of a planar surface of the second porous foam block (3-2-3-1).

Preferably, the absorbable core has a thickness of 0.8 mm to 6 mm.

Preferably, the absorbable core has a thickness of 0.8 mm to 2.5 mm.

A disposable absorption product comprising a liquid-permeable top sheet (1) at a top side of the disposable absorption product, a liquid-impermeable bottom sheet (2) at a bottom side of the disposable absorption product, and an absorbable core (3) according to any one of claims 1-8; the absorbable core (3) is sandwiched between the top sheet (1) and the bottom sheet (2).

The disposable absorption product further comprises a leakproof layer (4) which is bonded to an outer edge of the absorbable core (3) and is connected to an upper surface of the top sheet (1) and an upper surface of the bottom sheet (2).

Furthermore, a lower surface of the top sheet and the upper surface of the upper polyurethane foam layer, the lower surface of the upper polyurethane foam layer and an outer surface of the wrapping layer, the upper surface of the lower polyurethane foam layer and the inner surface of the wrapping layer, as well as the outer surface of the wrapping layer and the upper surface of the bottom sheet are each bonded by hot melt adhesive.

The absorbable core is still soft after lamination due to the use of soft and elastic polyurethane foam. As a result, the disposable absorption product of the present invention has super liquid absorbing capacity, and it is also soft and can be well attached to a body part that requires absorption, furthermore, it will not cause leakages such as side leakage.

An example of hydrophilic polyurethane porous foam is given below:

The hydrophilic polyurethane porous foam can be prepared by the following method, though not limited to the following method: taking 100 parts by weight of Hypol JM5004 from Dow chemical company, adding 100 parts by weight of aqueous solution having 1 wt % of surfactant into the Hypol JM5004, quickly stirring at room temperature to obtain a mixed emulsion, then resting the mixed emulsion flatly on a substrate, and then quickly covering the mixed emulsion by a non-woven fabric and an upper cover, waiting for 2-10 minutes for the mixed emulsion to foam and thus form the hydrophilic polyurethane porous foam; as such, a polyurethane foam layer is obtained. The surfactant used is Poloxamer 188 from BASF.

The upper polyurethane foam layer and the lower polyurethane foam layer are both made of hydrophilic polyurethane porous foam that allows downward liquid infiltration, thereby increasing liquid storage space.

Porosity is achieved by the gas generated during the foaming process of polyurethane which opens up many channels inside the polyurethane foam through which liquid can pass through, and some channels have their end points extended to a surface of the polyurethane foam to communicate with the external environment. Therefore, when liquid is poured from above the polyurethane foam to the surface of the polyurethane foam, the liquid may follow these channels which are in communication with one another and infiltrate deeply into the polyurethane foam or eventually pass through the polyurethane foam to reach beyond some other surfaces of the polyurethane foam. The channels vary in width and size, typically between 20 and 200 microns in diameter.

In this example, the lower surface of the top sheet (1) and the upper surface of the upper polyurethane foam layer (3-1), the lower surface of the upper polyurethane foam layer (3-1) and the outer surface of the wrapping layer (3-2), and the outer surface of the wrapping layer (3-2) and the upper surface of the bottom sheet (2) are each bonded together by hot melt adhesive.

Specific embodiments are given as follows:

Embodiment 1

Top sheet: 35 g/square meter of pure cotton perforated non-woven fabric;

Upper polyurethane foam layer: 50 g/square meter of polyurethane foam having a thickness of 0.5 mm is used, and 13 g/square meter of SSS non-woven fabric is arranged inside the polyurethane foam;

First sleeve body: 13 g/square meter of SSS hydrophilic non-woven fabric;

Particle layer: 100 g/square meter of super-absorbable polymer (SAP) particles, 19.2 g/square meter of citric acid particles, 8.4 g/square meter of sodium bicarbonate particles;

Lower polyurethane foam layer: having a thickness of 2.0 mm, specifically comprising 13 g/square meter of SSS non-woven fabric arranged inside 200 g/square meter of polyurethane foam;

Bottom sheet: 18 g/meter of PE breathable film;

Leakproof layer: 15 g/square meter of spun bond SMS water repellent cloth.

Property of the resulting absorption product: absorption of physiological saline up to saturation: 23 g/g;

Property of the resulting absorption product: locking of physiological saline up to saturation: 17 g/g;

Property of the resulting absorption product: absorption of artificial plasma up to saturation: 17 g/g;

Property of the resulting absorption product: locking of artificial plasma up to saturation: 12 g/g;

Property of the resulting absorption product: an original shape of the absorption product is resumed after 9 seconds when a 5 kg pressure is removed from the absorption product.

Embodiment 2

Top sheet: 23 g/square meter of hot air through perforated non-woven fabric;

Upper polyurethane foam layer: 50 g/square meter of polyurethane foam having a thickness of 0.5 mm is used, and 13 g/square meter of SSS non-woven fabric is arranged inside the polyurethane foam;

First sleeve body: 13 g/square meter of SSS hydrophilic non-woven fabric;

Particle layer: 80 g/square meter of SAP particles, 19.2 g/square meter of citric acid particles, 8.4 g/square meter of sodium bicarbonate particles;

Lower polyurethane foam layer: having a thickness of 1.0 mm, specifically comprising 13 g/square meter of SSS non-woven fabric arranged inside 100 g/square meter of polyurethane foam;

Bottom sheet: 18 g/meter of PE breathable film;

Leakproof layer: 15 g/square meter of spun bond SMS water repellent cloth.

Property of the resulting absorption product: absorption of physiological saline up to saturation: 25 g/g;

Property of the resulting absorption product: locking of physiological saline up to saturation: 19 g/g;

Property of the resulting absorption product: absorption of artificial plasma up to saturation: 18 g/g;

Property of the resulting absorption product: locking of artificial plasma up to saturation: 14 g/g;

Property of the resulting absorption product: an original shape of the absorption product is resumed after 15 seconds when a 5 kg pressure is removed from the absorption product.

Embodiment 3

Top sheet: 13 g/square meter of perforated spunbond non-woven fabric;

Upper polyurethane foam layer: 50 g/square meter of polyurethane foam having a thickness of 0.5 mm is used, and 13 g/square meter of SSS non-woven fabric is arranged inside the polyurethane foam;

First sleeve body: 18 g/square meter of toilet paper;

Particle layer: 70 g/square meter of SAP particles, 19.2 g/square meter of citric acid particles, 8.4 g/square meter of sodium bicarbonate particles;

Lower polyurethane foam layer: having a thickness of 0.5 mm, specifically comprising 13 g/square meter of SSS non-woven fabric arranged in 50 g/square meter of polyurethane foam;

Bottom sheet: 18 g/meter of PE breathable film;

Leakproof layer: 15 g/square meter of SMS spunbond water repellent cloth.

Property of the resulting absorption product: absorption of physiological saline up to saturation: 26 g/g;

Property of the resulting absorption product: locking of physiological saline up to saturation: 21 g/g;

Property of the resulting absorption product: absorption of artificial plasma up to saturation: 19 g/g;

Property of the resulting absorption product: locking of artificial plasma up to saturation: 14 g/g;

Property of the resulting absorption product: an original shape of the absorption product is resumed after 18 seconds when a 5 kg pressure is removed from the absorption product.

Embodiment 4

Top sheet: 13 g/square meter of PE perforated film;

Upper polyurethane foam layer: 30 g/square meter of polyurethane foam having a thickness of 0.3 mm is used, and 13 g/square meter of SSS non-woven fabric is arranged inside the polyurethane foam;

First sleeve body: 13 g/square meter of SSS hydrophilic non-woven fabric;

Particle layer: 70 g/square meter of SAP particles, 19.2 g/square meter of citric acid particles, 8.4 g/square meter of sodium bicarbonate particles;

Lower polyurethane foam layer: having a thickness of 0.5 mm, specifically comprising 13 g/square meter of SSS non-woven fabric arranged in 50 g/square meter of polyurethane foam;

Bottom sheet: 18 g/meter of PE breathable film;

Leakproof layer: 15 g/square meter of spun bond SMS water repellent cloth.

The properties of the resulting absorption article: absorption of physiological saline up to saturation: 28 g/g;

Property of the resulting absorption product: locking of saline up to saturation: 22 g/g;

Property of the resulting absorption product: absorption of artificial plasma up to saturation: 20 g/g;

Property of the resulting absorption product: locking of artificial plasma up to saturation: 14 g/g;

Property of the resulting absorption product: an original shape of the absorption product is resumed after 16 seconds when a 5 kg pressure is removed from the absorption product.

Cooling effect is also tested:

Cooling effect is tested according to the following steps: placing a sanitary absorption product according to the present invention stored under room temperature of 26° C. into a 35° C. oven for 1 hour, taking out the sanitary absorption product out of the oven, and then quickly laying the sanitary absorption product on a flat glass plate, and then pouring 5 mL of 37° C. artificial plasma quickly onto the sanitary absorption product in 5 seconds, after the artificial plasma is completely absorbed, applying and pressing a filter paper and a weight onto the sanitary absorption product, removing the filter paper and the weight from the sanitary absorption product after 5 minutes, and then measuring a surface temperature of the top sheet 1 and an increase in weight of the filter paper (reflecting reverse osmosis).

The test results are shown in the following table:

The comparative example 1 is a common 245 mm sanitary napkin under elegance series of brand SPACE7 purchased on the market.

| Tested subject | Absorption speed | Surface temperature | Reverse osmosis amount |
|---|---|---|---|
| Embodiment 1 | 12 seconds | 29.6° C. | 0.7 gram |
| Embodiment 2 | 11 seconds | 28.1° C. | 0.8 gram |
| Embodiment 3 | 11 seconds | 27.9° C. | 0.5 gram |
| Embodiment 4 | 10 seconds | 29.2° C. | 0.6 gram |
| Comparative example 1 | 9 seconds | 31.5° C. | 0.6 gram |

It can be seen that by adding the organic acid particles and the bicarbonate particles, and by mixing the organic acid particles, the bicarbonate particles and the high molecular weight super-absorbable polymer particles, the surface temperature of the absorption product is remarkably reduced under the same using time, thereby remarkably improve the stuffiness feeling when using the sanitary absorption product.

The preferred embodiments of the present invention have been described above, and the described embodiments are not intended to limit to the present invention. A person skilled in the art may make various changes and variations. Any modification, alternative configurations, or improvement made within the spirit and principle of the present invention should be included in the scope of protection of the present invention.

What is claimed is:

1. An absorbent core of a disposable absorption product, wherein the absorbent core comprises an upper part and a lower part; the upper part is an upper polyurethane foam layer which is liquid-permeable; the lower part is a wrapping layer which is capable of absorbing liquid; the wrapping layer comprises an outer part and an inner part; the outer part is a first sleeve body which is liquid-impermeable; the inner part is an accommodating cavity; a lower polyurethane foam layer and a particle layer are provided inside the accommodating cavity, wherein the particle layer is distributed on an upper surface of the lower polyurethane foam layer, and the particle layer contains a mixture of resin particles, organic acid particles, and anhydrous bicarbonate particles; the resin particles are distributed on the upper surface of the lower polyurethane foam layer in an amount of 50-150 g/m$^2$, the organic acid particles are distributed on the upper surface of the lower polyurethane foam layer in an amount of 15-25 g/m$^2$, and the anhydrous bicarbonate particles are distributed on the upper surface of the lower polyurethane foam layer in an amount of 8-16 g/m$^2$.

2. The absorbent core according to claim 1, wherein a molar ratio of the organic acid particles to the anhydrous bicarbonate particles is 1:1; the resin particles are super-absorbent polymer resin particles.

3. The absorbent core according to claim 1, wherein a lower surface of the upper polyurethane foam layer and/or the upper surface of the lower polyurethane foam layer is/are undulated.

4. The absorbent core according to claim 1, wherein the upper polyurethane foam layer comprises a continuous and uniform first porous foam block made of hydrophilic polyurethane material, and a first non-woven fabric layer provided inside the first porous foam block and extending through said first porous foam block along an extending direction of a planar surface of the first porous foam block.

5. The absorbent core according to claim 1, wherein said upper polyurethane foam layer is provided with a plurality of through holes penetrating through an upper surface and a lower surface thereof.

6. The absorbent core according to claim 1, wherein the lower polyurethane foam layer comprises a continuous and uniform second porous foam block made of hydrophilic polyurethane material, and a second non-woven fabric layer provided inside the second porous foam block and extending through said second porous foam block along an extending direction of a planar surface of the second porous foam block.

7. The absorbent core according to claim 1, wherein the absorbent core has a thickness of 0.8 mm to 6 mm.

8. The absorbent core according to claim 7, wherein the absorbent core has a thickness of 0.8 mm to 2.5 mm.

9. A disposable absorption product, comprising a liquid-permeable top sheet at a top side of the disposable absorption product, a liquid-impermeable bottom sheet at a bottom side of the disposable absorption product, and an absorbent core according to any one of claims 1-8; the absorbent core is sandwiched between the top sheet and the bottom sheet.

10. The disposable absorption product of claim 9, further comprising a leakproof layer which is bonded to an outer edge of the absorbent core and is connected to an upper surface of the top sheet and an upper surface of the bottom sheet.

* * * * *